(12) United States Patent
Changaris et al.

(10) Patent No.: US 10,105,332 B1
(45) Date of Patent: *Oct. 23, 2018

(54) METHODS AND COMPOSITION FOR SUPPRESSION OF DEEP SEATED FUNGAL GROWTH ON SKIN

(71) Applicant: David Changaris, Louisville, KY (US)

(72) Inventors: David G. Changaris, Louisville, KY (US); Kelly Sullivan, Louisville, KY (US)

(73) Assignee: David G. Changaris, Louisville, KY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/793,978

(22) Filed: Oct. 25, 2017

Related U.S. Application Data

(63) Continuation of application No. 15/788,798, filed on Oct. 19, 2017, now Pat. No. 10,052,300.

(51) Int. Cl.
| | | |
|---|---|---|
| *A61K 31/455* | (2006.01) | |
| *A61K 31/20* | (2006.01) | |
| *A61K 31/195* | (2006.01) | |
| *A61K 31/201* | (2006.01) | |
| *A61K 31/198* | (2006.01) | |
| *A61K 31/202* | (2006.01) | |

(52) U.S. Cl.
CPC .......... *A61K 31/201* (2013.01); *A61K 31/198* (2013.01); *A61K 31/202* (2013.01); *A61K 31/455* (2013.01)

(58) Field of Classification Search
CPC ..... A61K 31/455; A61K 31/20; A61K 31/195
USPC ........................................ 514/355, 560, 561
See application file for complete search history.

(56) References Cited

U.S. PATENT DOCUMENTS

| | | | |
|---|---|---|---|
| 6,245,811 B1 * | 6/2001 | Horrobin | .............. C07C 69/007 |
| | | | 514/546 |
| 7,074,418 B2 | 7/2006 | Changaris | |
| 7,897,160 B2 | 3/2011 | Changaris | |
| 9,549,550 B2 | 1/2017 | Changaris | |
| 2013/0108585 A1 * | 5/2013 | Mogna | ................... A61K 35/74 |
| | | | 424/93.4 |
| 2014/0113968 A1 * | 4/2014 | Monster | ................. C11C 1/005 |
| | | | 514/560 |
| 2016/0022622 A1 * | 1/2016 | Remmereit | ............ A61K 31/19 |
| | | | 514/560 |
| 2017/0079945 A1 | 3/2017 | Changaris | |

\* cited by examiner

*Primary Examiner* — Raymond J Henley, III
(74) *Attorney, Agent, or Firm* — Steve Witters; Witters & Associates

(57) ABSTRACT

The present disclosure relates to methods and compositions for suppressing the growth of fungus on selected areas of the skin. A composition for suppressing deep seated fungal growth comprising conjugated linoleic acid, Punicic acid, or combination thereof, and niacinamide and L-aspartic acid is provided herein. Methods of making and using the composition are also presently provided.

20 Claims, 3 Drawing Sheets

3/4/2017 7:30pm
Before application of CLA-
Aspartate-Niacinamide

3/6/2017 11:30 PM
Itching-redness resolved at
24-36 hrs scaling shown at
51 hrs here 3/9/2017 11:30 PM
Subtotal return to normal;
salve stopped 5/30/2017 6PM
Resolution of redness persisting
after 10weeks

METHODS AND COMPOSITION FOR SUPPRESSION OF DEEP SEATED FUNGAL GROWTH ON SKIN

CROSS-REFERENCE TO RELATED APPLICATIONS

This application is a Continuation of U.S. patent application Ser. No. 15/788,798, filed on Oct. 19, 2017, which is incorporated herein by reference in its entirety.

FIELD OF THE DISCLOSURE

Aspects of the present disclosure generally relate to methods and compositions for suppressing deep seated fungal growth on selected areas of the skin.

BACKGROUND

Background information is for informational purposes only and does not necessarily admit that subsequently mentioned information and publications are prior art.

People are cognizant with the notion of microbes (i.e., microorganisms such as bacteria and fungi) as being potentially hazardous and their transmission from person to person. People come into contact with these potentially hazardous microbes on a daily basis. Once in contact with human hands, these microbes or fungi may be passed from individual to individual and, thus, may contribute to the spread of infectious and contagious diseases. One of the most common ways of mitigating infection or transmitting such microbes or fungi is by washing or applying emollients.

SUMMARY

Methods and a composition for suppressing deep seated fungal growth comprising conjugated linoleic acid, Punicic acid, or combination thereof, and niacinamide as well as L-aspartic acid is provided herein.

According to one aspect of the present disclosure, a method for suppressing deep seated fungal growth in or on a selected area of skin is disclosed. The method comprises preparing a composition having at least one of conjugated linoleic acid and punicic acid, or combination thereof. Niacinamide and L-aspartic acid are added to the composition. An area of the skin having the deep seated fungal growth is selected for application of the composition. The prepared composition is applied to the selected area of the skin and thereby suppresses the deep seated fungal growth in or on the selected area of skin.

In another aspect of the present disclosure, a method of preparing a composition for suppressing deep seated fungal growth is disclosed. The method comprises providing an amount of conjugated linoleic acid, Punicic acid, or combination thereof. An amount of niacinamide is added to the provided conjugated linoleic acid, Punicic acid, or combination thereof. An amount of L-aspartic acid is added to the conjugated linoleic acid, punicic acid, or combination thereof, and the niacinamide.

In a further aspect, a composition for suppressing deep seated fungal growth is disclosed. The composition comprises 1) conjugated linoleic acid, punicic acid, or combination thereof; 2) niacinamide; and 3) L-aspartic acid.

These and other features, aspects and advantages of the present disclosure will become better understood with reference to the following drawings, description and claims.

BRIEF DESCRIPTIONS OF THE DRAWINGS

DETAILED DESCRIPTION

Figure 1:
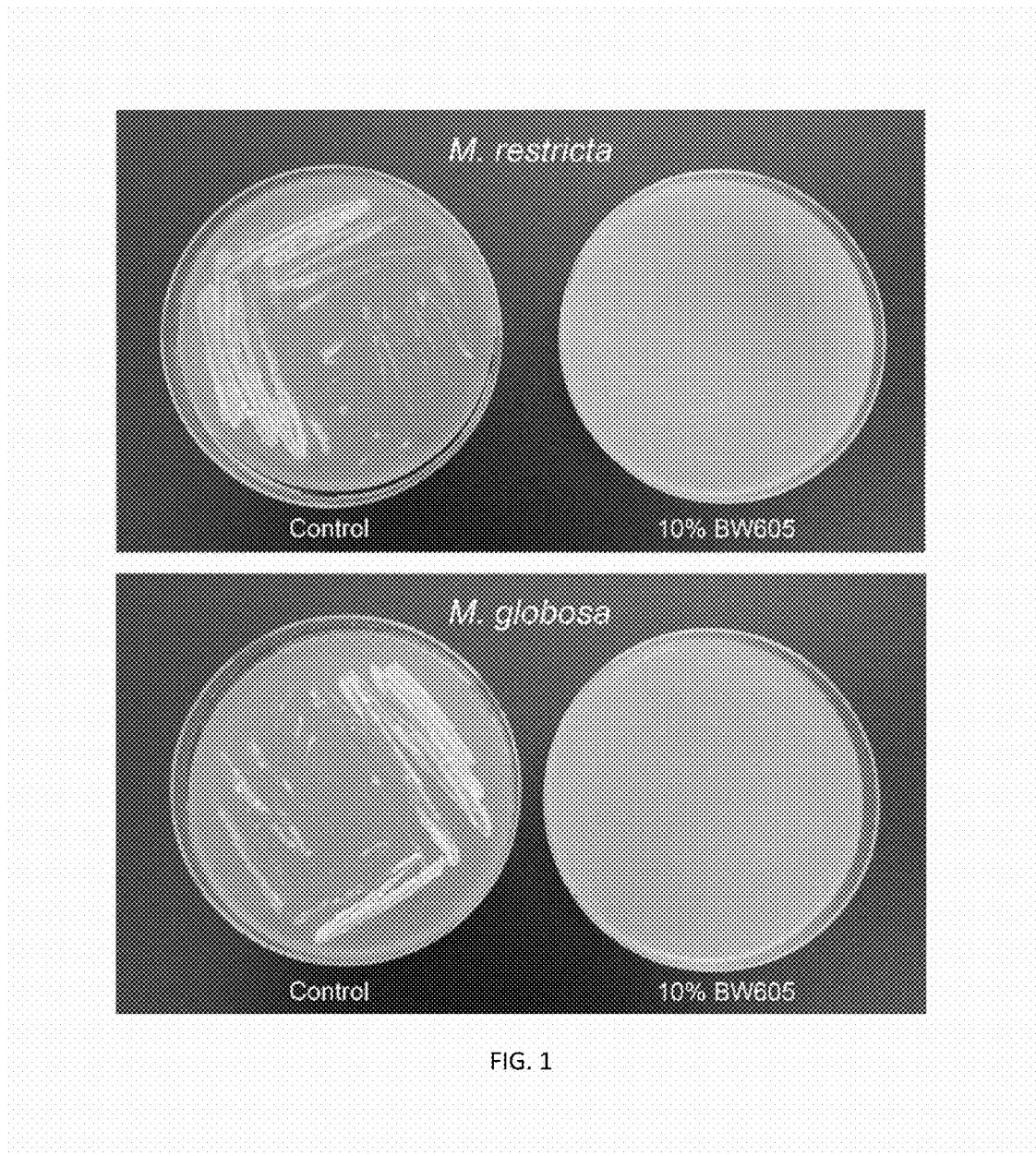
FIG. 1 shows *M. restricta* and *M. globosa* growth on solid media.

The following detailed description is not to be taken in a limiting sense, but is made merely for the purpose of illustrating the general principles of the disclosure, since the scope of the disclosure is best defined by the appended claims.

Various inventive features are described below that can each be used independently of one another or in combination with other features. However, any single inventive feature may not address any of the problems discussed above or may only address a subset of the problems discussed above. Further, one or more of the problems discussed above may not be fully addressed by any of the features described below.

Aspects of the present disclosure generally relate to methods and compositions for suppressing deep seated fungal growth in or on selected areas of the skin. For example, the presently disclosed methods and compositions may be used as an active treatment of seborrheic dermatitis. In at least one embodiment, the presently composition inhibits the growth of *Malassezia*.

*Malassezia* sp. have been associated with atopic dermatitis, seborrheic dermatitis, *pityriasis versicolor*, and *Malassezia* folliculitis. Among the various species *M. globosa* and *M. restricta* are clinically associated with seborrheic dermatitis or dandruff. *Malassezia* sp. are ubiquitous across the human microbiome. Herein, we disclose the ability of a novel cosmetic formulation or composition to inhibit fungal growth.

The presently disclosed composition may comprise naturally occurring materials. In at least one embodiment, the presently disclosed composition consists only of naturally occurring materials. The composition may comprise a plurality of active materials and a synergistic effect of the active materials may be realized for the suppression of deep seated fungal growth.

In at least one embodiment of the present disclosure, a composition for suppressing deep seated fungal growth comprises conjugated linoleic acid, punicic acid, or combination thereof. The composition additionally comprise niacinamide and L-aspartic acid. A combination of active ingredients of 1) conjugated linoleic acid and/or punicic acid, 2) niacinamide, and 3) L-aspartic acid may provide a composition that is substantially more effective for suppressing deep seated fungal growth than any of the three active ingredients alone. The increased effectiveness of the combination of linoleic acid and/or punicic acid, niacinamide, and L-aspartic acid in suppressing deep seated fungal growth may be due to a synergistic effect among the active materials.

Conjugated fatty acids and methods of using as well as methods of preparing materials comprising conjugated fatty acids are disclosed in U.S. Pat. No. 7,074,418, U.S. Pat. No. 7,897,160 and U.S. Pat. No. 9,549,550, each of which are incorporated by reference herein. U.S. Pat. Nos. 9,549,550, 7,897,160, and 7,074,418 are incorporated by reference in their entirety herein, except for the prosecution thereof and words relating to the opinions and judgments of the author and words not directly relating to the technical details of the description of the aspects therein, are not incorporated by reference. The purpose of incorporating these publications is solely to provide additional information relating to technical features of one or more aspects, which information may not be completely disclosed in the wording in the pages of this application. The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the above-mentioned words in this sentence, when not used to describe technical features of one or more aspects, are not to be incorporated by reference herein.

Conjugated fatty acids result from the shift of a double bond in the long chained fatty acid with two double bonds, predominantly in safflower oil and sunflower oil, the diene C18, linoleic acid. The linoleic acid molecule in its natural plant expressed state has two double bonds separated by a single carbon, which is saturated with hydrogen. Thus the molecules C9, C11 and C10, C12 linoleic acids represent two of the most common linoleic acids.

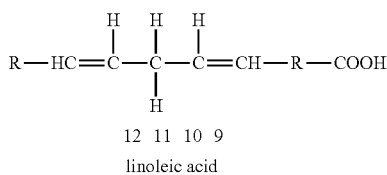

12  11  10  9
linoleic acid

This unconjugated form permits the aliphatic and carboxyl ends to rotate about the C10 or C11. The conjugated form derived from processing has the general formula (C18:2 c9, t11; and C18:2 t10 c12):

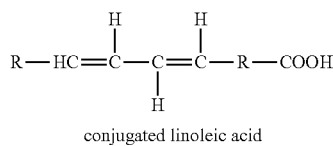

conjugated linoleic acid

There are some 28 isomers of CLA. When the double bonds are close as in CLA, the central double bonds resemble a "boomerang" with a hydrophobic center that allows for the orientation of amphipathic molecules and the semi-rigidity of the emulsion. Both cis and trans molecules may contribute to the processes and compositions disclosed herein.

Both CLA and steric acid contain 18 carbons. In general the majority of cell walls are a bi-lipid layer comprised to two adjacent 18 carbon Stearic acids. Membranes comprised of both CLA and Stearic acid would lack a coherent rigid cell wall essential to the integrity of bacteria and fungi. CLA may have the properties for reducing bacterial and/or fungal growth by interfering with the normal metabolism of C-18 molecules of pathogenic bacteria and fungi.

The CLA of the present disclosure may be esterified with methyl, ethyl, or longer radicals. The CLA of the present disclosure may be sulfated or etholxylated sulfate or similar negatively charged moiety.

Punicic acid (also called trichosanic acid) is a polyunsaturated fatty acid, 18:3 cis-9, trans-11, cis-13. It is named for the pomegranate and is obtained from pomegranate seed oil. It is also found in the seed oils of snake gourd. Punicic acid is chemically similar to the conjugated linoleic acids, or CLA. Punicic acid has three double bonds whereas CLA has two double bonds.

Niacinamide, also known as nicotinamide (NAA), is a vitamin found in food, used as a dietary supplement, and used as a medication. As a supplement, it is used by mouth to prevent and treat pellagra (niacin deficiency).

L-aspartic acid (L-ASP) is one of the non-essential amino acids in human protein ordinarily used in cosmetic products. L-aspartic acid is found in animals and plants, especially in sugar cane and sugar beets. Aspartic Acid has an overall negative charge and plays an important role in the synthesis of other amino acids and in the citric acid and urea cycles.

In at least one embodiment of the present disclosure, a composition for suppressing fungal growth comprises naturally occurring materials acting as an active treatment. For example, the composition may be used to treat seborrheic dermatitis. The composition may comprise CLA and isomers, punicic acid, or both. The composition may inhibit the growth of *Malassezia* species known to cause seborrheic dermatitis or seborrhea. The pharmaceutical product when coupled with a diet rich in conjugated linoleic acid may further reduce the symptoms of skin dermatitis.

The present disclosure relates to a method and pharmacologic preparations, compositions, or natural compositions, which may be used in the dermatologic field to treat seborrheic dermatitis by direct skin application. Seborrhea affects 4-31% of the general population. While no generally agreed upon etiology is accepted, most agree *Malassezia* species figure prominently in the maintenance of symptoms. This fungus requires saturated fats to grow. Antifungal agents such as Ketoconazol are the mainstream of treatment for seborrhea.

The presently disclosed compositions and methods show activity against 3 species of *Malassezia*, namely *M. globosa*, *M. restricta* and *M. furfur*. It is presently disclosed that Nicotinamide (vitamin B3 amide) and aspartic acid (amino acid) have additive capacity in efficacy. It is also presently disclosed that nicotinamide has a direct inhibitory action on *Malassezia* species. It is presently shown that Aspartic acid alone has specific impact on reducing the growth of three *Malassezia* species.

In at least one embodiment of the present disclosure, a composition for suppressing deep seated fungal growth comprises conjugated linoleic acid, Punicic acid, or combination thereof; niacinamide; and L-aspartic acid. The composition may comprise the conjugated linoleic acid, punicic acid, or combination thereof, in a range between about 0.5% to about 70%, or in a range between about 0.5% to about 30%. A balance of the composition may comprise inert or non-acting materials such as water and/or one or more pharmacologically acceptable carriers.

In at least one other embodiment of the present disclosure, a composition for suppressing deep seated fungal growth comprises conjugated linoleic acid, Punicic acid, or combination thereof; niacinamide; and L-aspartic acid. The composition may comprise the niacinamide in a range from about 0.1% to about 15%, or in a range from about 0.1% to about 10%. A balance of the composition may comprise inert or non-acting materials such as water and/or one or more pharmacologically acceptable carriers.

In at least one other embodiment of the present disclosure, a composition for suppressing deep seated fungal growth comprises conjugated linoleic acid, Punicic acid, or combination thereof; niacinamide; and L-aspartic acid. The composition may comprise the L-aspartic acid in a range from about 0.1% to about 15%, or in a range from about 0.1% to about 10%.

EXAMPLES

Example 1

In Vitro Materials and Methods:
Organisms.
*Malassezia* strains, *M. restricta* MYA-4611 and *M. globosa*, were obtained from American Type Culture Collection, ATCC, of Manassas, Va. Strain identifications were confirmed using previously established phenotypic culture-based methods. The presently disclosed composition was obtained from Ceela Naturals, of Louisville, Ky. All other materials were obtained from HiMedia or Sigma Aldrich unless otherwise mentioned.

Culture Media.
Cultures of *M. restricta* and *M. globosa* were grown on Modified Leeming and Notman Agar (MLNA) composed of (per 1 L) Bacteriological peptone (10 g), Glucose (10 g), Yeast extract (2.0 g), desiccated Ox bile (8.0 g), Glycerol (10 mL), Glycerol monostearate (0.5 g), Tween 60 (5.0 mL), Olive oil (20 mL), Agar (15 g) and sterilized by autoclaving. For liquid media, Modified Leeming and Notman Broth (MLNB), agar was omitted. Sabouraud Dextrose Agar (SDA, Acumedia) was used as a negative control. CHROMagar *Malassezia* media (DRG International, Springfield, N.J.) was used for strain identification.

Procedure.
Experimental solid media was supplemented with 2%-10% of an embodiment of the presently disclosed composition. In the present example, an example composition comprising 0.5% niacinamide (Pure Bulk), 0.46% L-Asp (Pure Bulk), and 1.5% conjugated linoleic acid (Stepan) was prepared and used. Separately, experimental solid media were individually supplemented 0.5% niacinamide, 0.46% L-Asp, and 1.5% conjugated linoleic acid. Additionally, a control solid media was not supplemented. The control and supplemented media were assessed for growth after 5 days. All experiments were performed in triplicate.

Determination of cell viability was based on cfu/mL from liquid cultures grown at 30° C. with shaking at 150 rpm. A single colony was used to inoculate a 10 mL starter culture in MLNB, which was grown to saturation (5 days). Starter cultures were diluted into a 125 mL MLNB culture to obtain an $OD_{600}=0.1$. Experimental cultures were supplemented with nothing (control), 2%-10% of the example composition, 0.5% niacinamide, 0.46% L-Asp, or 1.5% conjugated linoleic acid. At appropriate time intervals (0 h, 24 h, 48 h, 72 h, and 168 h) 1 mL aliquots of the cell suspension were withdrawn and plated on MLNA. All the experiments were performed in duplicate.

Figure 2:
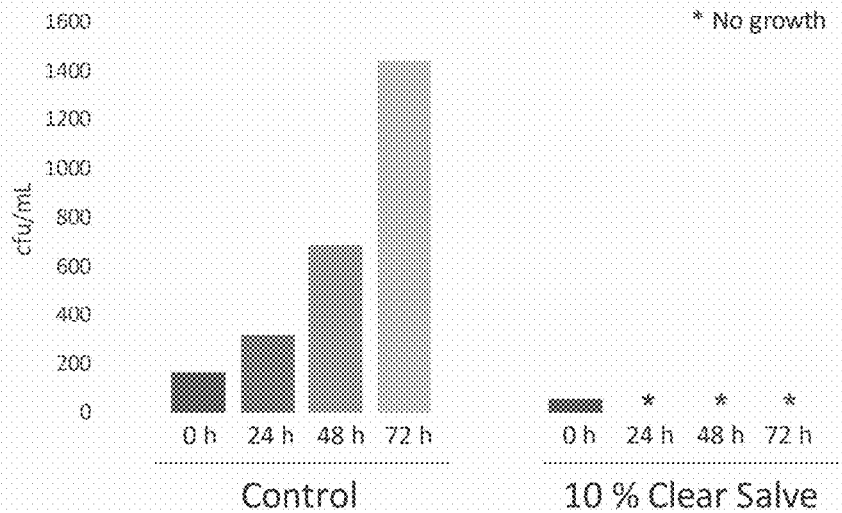
FIG. 2 shows *M. restricta* and *M. globosa* growth in liquid MLNB media.

Results:
FIGS. 1 and 2 show that *M. globosa* and *M. restricta* are inhibited by a 10% (v/v) supplementation of the example composition. The lowest effective concentration of the example composition was shown to be 5% (v/v). Specifically FIG. 1 shows *M. restricta* and *M. globosa* growth on solid media. Top panel: *M. restricta* on MLNA media (left) and MLNA media supplemented with 10% (v/v) of the example composition (right). Bottom panel: *M. globosa* on MLNA media (left) and MLNA media supplemented with 10% (v/v) of the example composition. FIG. 1 shows that neither *Malassezia* sp. can grow on the example composition supplemented media.

Specifically, FIG. 2 shows *M. restricta* and *M. globosa* growth in liquid MLNB media. Only averaged cfu/mL of both *Malassezia* sp. is shown. Growth was measured at the selected time intervals of 0, 24 hours, 48 hours, and 72 hours. The graph on the left shows that exponential growth was exhibited in the control having no supplementation. The graph on the right shows that the sample having a 10% supplementation of the example composition exhibited no growth after 24 hours.

Figure 3:
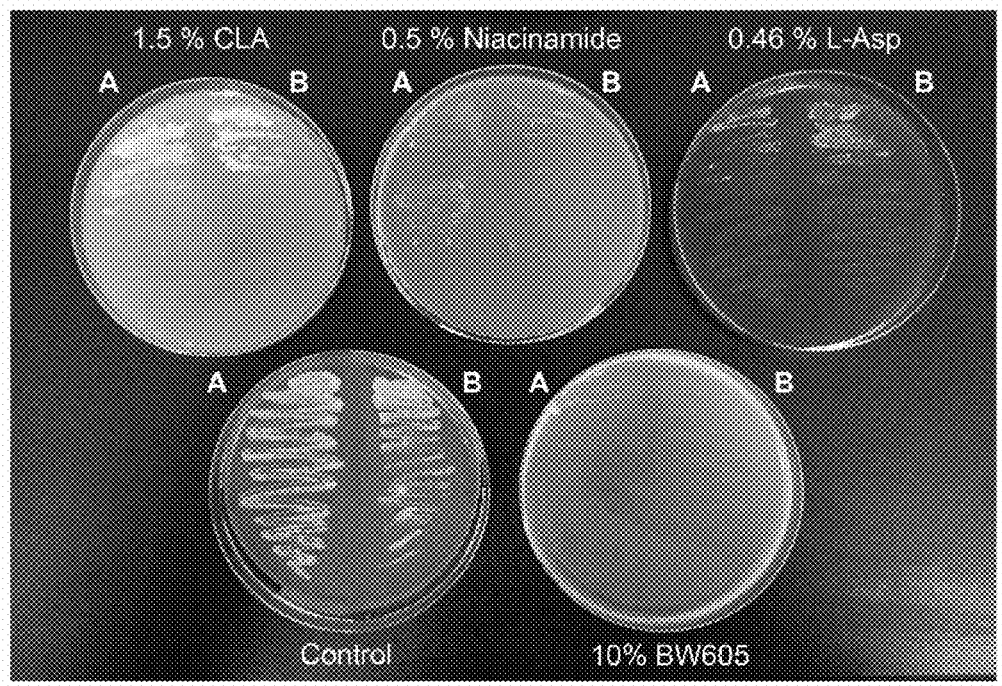
FIG. 3 shows *M. restricta* and *M. globosa* growth on solid media with composition and individual component supplementation.

The synergistic effect of ingredients in the example composition is shown to provide effective inhibition. As shown in FIG. 3 and Tables 1 and 2, below, each component alone may not be sufficient to fully suppress growth on solid or liquid media.

FIG. 3 shows *M. restricta* and *M. globosa* growth on solid media with individual component supplementation of 1.5% CLA, 0.5% niacinamide, and 0.46% L-Asp, top row respectively. A) is the left portion of the plate with *M. restricta* and B) is the right portion of the plate having *M. globosa*. All individual components support some growth as shown in the plates in the top row of FIG. 3. The 10% (v/v) supplementation of the example composition shows that example composition does not support growth as shown in the bottom right plate in FIG. 3. The bottom left plate is the control having no supplementation and shows substantially more growth than each of the other plates.

TABLE 1

*M. restricta* growth in liquid MLNB media.

| | MLNB (cfu/mL) | 10% THE PRESENTLY DISCLOSED COMPOSITION (cfu/mL) | 0.5% Niacinamide (cfu/mL) | 0.46% L-Asp (cfu/mL) | 1.5% CLA (cfu/mL) |
|---|---|---|---|---|---|
| t = 0 | $2.5 \times 10^2$ | | | | |
| t = 24 h | $4.6 \times 10^2$ | 0 | 20 | 15 | 7 |
| t = 48 h | $8.5 \times 10^2$ | 0 | 5 | 11 | 0 |
| t = 72 h | $1.7 \times 10^3$ | 0 | 0 | 10 | 0 |
| t = 168 h | $2.0 \times 10^5$ | 0 | 0 | 14 | 0 |

TABLE 2

*M. globosa* growth in liquid MLNB media.

| | MLNB (cfu/mL) | 10% THE PRESENTLY DISCLOSED COMPOSITION (cfu/mL) | 0.5% Niacinamide (cfu/mL) | 0.46% L-Asp (cfu/mL) | 1.5% CLA (cfu/mL) |
|---|---|---|---|---|---|
| t = 0 | $1.1 \times 10^2$ | | | | |
| t = 24 h | $2.4 \times 10^2$ | 0 | 2 | 14 | 2 |
| t = 48 h | $6.4 \times 10^2$ | 0 | 0 | 10 | 0 |
| t = 72 h | $1.2 \times 10^3$ | 0 | 0 | 6 | 0 |
| t = 168 h | $2.2 \times 10^5$ | 0 | 0 | 1 | 0 |

Conclusion:
A supplementation of a 10% concentration of the example composition comprising 1.5% CLA, 0.5% niacinamide (Pure Bulk), and 0.46% L-Asp (Pure Bulk) is sufficient to inhibit the growth of *M. globosa* and *M. restricta* in vitro.

Example 2

In Vivo

A first test composition comprising 15% CLA and 4.6% L-Asp was prepared. An area of the skin of a subject having the deep seated fungal growth was selected. The first test composition was applied onto the selected area of skin daily and the subject was examined at selected time intervals. After 10 days, the subject exhibited no visual change as shown in the upper left of FIG. 4.

A second test composition comprising 15% CLA, 5% niacinamide, and 4.6% L-Asp was prepared. The same area of the skin of the same subject having the deep seated fungal growth was selected, like the application of the first test composition. The second test composition was applied in the same manner as the first composition and the subject was again examined at selected time intervals. The results are shown in FIG. 4.

Figure 4:
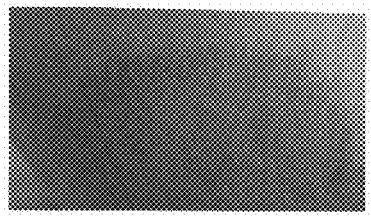
FIG. 4 shows in vivo results of an application of the presently disclosed composition.
Figure 4:
Figure 4:
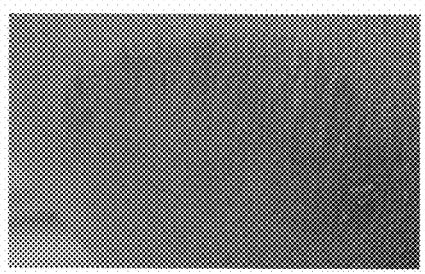
Figure 4:
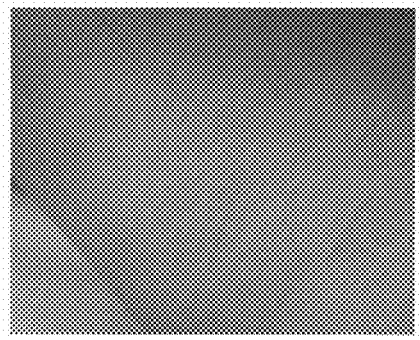

With the application of the second composition having CLA, niacinamide, and L-Asp, the subject showed a clear reduction in itching and burning at 24 hours or less and clear visual evidence of healing is shown in FIG. 4, upper right, at 51 hours or less. The subject returned to normal in about 5 days, as shown in the lower left picture in FIG. 5, and the resolution of fungal growth persisted, as shown in the lower right picture in FIG. 5.

The results of the application of the first composition compared with the application of the second composition demonstrates the synergistic effect of CLA, niacinamide, and L-Asp with the in vivo application.

One feature or aspect of an illustrative example is believed at the time of the filing of this patent application to possibly reside broadly in a method for suppressing deep seated fungal growth in or on a selected area of skin, the method comprising the steps of: preparing a composition comprising: at least one of conjugated linoleic acid and punicic acid; niacinamide; and L-aspartic acid; selecting an area of the skin having the deep seated fungal growth; and applying the prepared composition to the selected area of the skin and thereby suppressing the deep seated fungal growth in or on the selected area of skin.

Another feature or aspect of an illustrative example is believed at the time of the filing of this patent application to possibly reside broadly in a method for suppressing deep seated fungal growth in or on a selected area of skin wherein the deep seated fungal growth is *Malassezia* sp.

Yet another feature or aspect of an illustrative example is believed at the time of the filing of this patent application to possibly reside broadly in a method for suppressing deep seated fungal growth in or on a selected area of skin wherein the prepared composition comprises the conjugated linoleic acid, punicic acid, or combination thereof, at a concentration between about 0.5% to about 70%.

Still another feature or aspect of an illustrative example is believed at the time of the filing of this patent application to possibly reside broadly in a method for suppressing deep seated fungal growth in or on a selected area of skin wherein the prepared composition comprises niacinamide at a concentration between about 0.1% to about 15%.

A further feature or aspect of an illustrative example is believed at the time of the filing of this patent application to possibly reside broadly in a method for suppressing deep seated fungal growth in or on a selected area of skin wherein the prepared composition comprises the L-aspartic acid at a concentration between about 0.1% to about 15%.

Yet another feature or aspect of an illustrative example is believed at the time of the filing of this patent application to possibly reside broadly in a method for suppressing deep seated fungal growth in or on a selected area of skin wherein the prepared composition comprises metal ions.

Still another feature or aspect of an illustrative example is believed at the time of the filing of this patent application to possibly reside broadly in a method for suppressing deep seated fungal growth in or on a selected area of skin wherein the prepared composition the metal ions are selected from the group consisting of sodium, potassium, magnesium, calcium, and combinations thereof.

A further feature or aspect of an illustrative example is believed at the time of the filing of this patent application to possibly reside broadly in a method for suppressing deep seated fungal growth in or on a selected area of skin wherein the suppressing of the deep seated fungal growth is achieved to an extent to be detected in less than 24 hours.

Another feature or aspect of an illustrative example is believed at the time of the filing of this patent application to possibly reside broadly in a method for suppressing deep seated fungal growth in or on a selected area of skin wherein the step of providing at least one of conjugated linoleic acid and punicic acid comprises providing conjugated linoleic acid.

Yet another feature or aspect of an illustrative example is believed at the time of the filing of this patent application to possibly reside broadly in a method of preparing a composition for suppressing deep seated fungal growth comprising the steps of: providing an amount of conjugated linoleic acid, Punicic acid, or combination thereof; adding an amount of niacinamide to the provided conjugated linoleic acid, Punicic acid, or combination thereof; and adding an amount of L-aspartic acid to the conjugated linoleic acid, punicic acid, or combination thereof, and the niacinamide.

One feature or aspect of an illustrative example is believed at the time of the filing of this patent application to possibly reside broadly in a method of preparing a composition for suppressing deep seated fungal growth wherein the amount of conjugated linoleic acid, punicic acid, or combination thereof, is provided in an amount to provide a concentration of the conjugated linoleic acid, punicic acid, or combination thereof in the composition between about 0.5% to about 70%.

Another feature or aspect of an illustrative example is believed at the time of the filing of this patent application to possibly reside broadly in a method of preparing a composition for suppressing deep seated fungal growth wherein the amount of niacinamide is added in an amount to provide a concentration of the niacinamide in the composition between about 0.1% to about 15%.

Yet another feature or aspect of an illustrative example is believed at the time of the filing of this patent application to possibly reside broadly in a method of preparing a composition for suppressing deep seated fungal growth wherein the amount of L-aspartic acid is added in an amount to provide a concentration of the L-aspartic acid in the composition between about 0.1% to about 15%.

A further feature or aspect of an illustrative example is believed at the time of the filing of this patent application to possibly reside broadly in a method of preparing a composition for suppressing deep seated fungal growth further comprising adding metal ions to the composition.

Another feature or aspect of an illustrative example is believed at the time of the filing of this patent application to possibly reside broadly in a method of preparing a composition for suppressing deep seated fungal growth wherein the added metal ions are selected from the group consisting of sodium, potassium, magnesium, calcium, and combinations thereof.

Yet another feature or aspect of an illustrative example is believed at the time of the filing of this patent application to possibly reside broadly in a method of preparing a composition for suppressing deep seated fungal growth wherein the amount of conjugated linoleic acid, punicic acid, or combination thereof, is provided in an amount to provide a concentration of the conjugated linoleic acid, punicic acid, or combination thereof in the composition between about 0.5% to about 30%.

Still another feature or aspect of an illustrative example is believed at the time of the filing of this patent application to possibly reside broadly in a method of preparing a composition for suppressing deep seated fungal growth wherein the amount of niacinamide is added in an amount to provide a concentration of the niacinamide in the composition between about 0.1% to about 10%.

A further feature or aspect of an illustrative example is believed at the time of the filing of this patent application to possibly reside broadly in a method of preparing a composition for suppressing deep seated fungal growth wherein the amount of L-aspartic acid is added in an amount to provide a concentration of the L-aspartic acid in the composition of between about 0.1% to about 10%.

Another feature or aspect of an illustrative example is believed at the time of the filing of this patent application to possibly reside broadly in a composition for suppressing deep seated fungal growth comprising: conjugated linoleic acid, Punicic acid, or combination thereof; niacinamide; and L-aspartic acid.

Yet another feature or aspect of an illustrative example is believed at the time of the filing of this patent application to possibly reside broadly a composition for suppressing deep seated fungal growth comprising conjugated linoleic acid, punicic acid, or combination thereof, at a concentration between about 0.5% to about 30%.

Still another feature or aspect of an illustrative example is believed at the time of the filing of this patent application to possibly reside broadly in a composition for suppressing deep seated fungal growth comprising niacinamide at a concentration between about 0.1% to about 10%.

A further feature or aspect of an illustrative example is believed at the time of the filing of this patent application to possibly reside broadly in a composition for suppressing deep seated fungal growth comprising L-aspartic acid at a concentration between about 0.1% to about 10%.

It should be understood that the foregoing relates to exemplary aspects of the disclosure and that modifications may be made without departing from the spirit and scope of the disclosure as set forth in the following claims.

The invention claimed is:

1. A method for suppressing deep seated fungal growth in or on a selected area of skin, the method comprising the steps of:
preparing a composition comprising:
at least one of conjugated linoleic acid and punicic acid;
niacinamide; and
L-aspartic acid;
selecting an area of the skin having the deep seated fungal growth; and
applying the prepared composition to the selected area of the skin and thereby suppressing the deep seated fungal growth in or on the selected area of skin.

2. The method of claim 1, wherein the deep seated fungal growth is *Malassezia* sp.

3. The method of claim 1, wherein the prepared composition comprises the conjugated linoleic acid, punicic acid, or combination thereof, at a concentration between about 0.5% to about 70%.

4. The method of claim 1, wherein the prepared composition comprises niacinamide at a concentration between about 0.1% to about 15%.

5. The method of claim 1, wherein the prepared composition comprises the L-aspartic acid at a concentration between about 0.1% to about 15%.

6. The method of claim 1, wherein the prepared composition comprises metal ions.

7. The method of claim 6, wherein the prepared composition the metal ions are selected from the group consisting of sodium, potassium, magnesium, calcium, and combinations thereof.

8. The method of claim 7, wherein the suppressing of the deep seated fungal growth is achieved to an extent to be detectable in less than 24 hours.

9. The method of claim 1, wherein the step of providing at least one of conjugated linoleic acid and punicic acid comprises providing conjugated linoleic acid.

10. A method of preparing a composition for suppressing deep seated fungal growth comprising the steps of:
providing an amount of conjugated linoleic acid, Punicic acid, or combination thereof;
adding an amount of niacinamide to the provided conjugated linoleic acid, Punicic acid, or combination thereof; and
adding an amount of L-aspartic acid to the conjugated linoleic acid, punicic acid, or combination thereof, and the niacinamide.

11. The method of claim 10, wherein the amount of conjugated linoleic acid, punicic acid, or combination thereof, is provided in an amount to provide a concentration of the conjugated linoleic acid, punicic acid, or combination thereof in the composition between about 0.5% to about 70%.

12. The method of claim 10, wherein the amount of niacinamide is added in an amount to provide a concentration of the niacinamide in the composition between about 0.1% to about 15%.

13. The method of claim 10, wherein the amount of L-aspartic acid is added in an amount to provide a concentration of the L-aspartic acid in the composition between about 0.1% to about 15%.

14. The method of claim 10 further comprising adding metal ions to the composition.

15. The method of claim 14, wherein the added metal ions are selected from the group consisting of sodium, potassium, magnesium, calcium, and combinations thereof.

16. The method of claim 11, wherein the amount of conjugated linoleic acid, punicic acid, or combination thereof, is provided in an amount to provide a concentration of the conjugated linoleic acid, punicic acid, or combination thereof in the composition between about 0.5% to about 30%.

17. The method of claim 12, wherein the amount of niacinamide is added in an amount to provide a concentration of the niacinamide in the composition between about 0.1% to about 10%.

18. The method of claim 13, wherein the amount of L-aspartic acid is added in an amount to provide a concentration of the L-aspartic acid in the composition of between about 0.1% to about 10%.

19. A composition for suppressing deep seated fungal growth comprising:
- conjugated linoleic acid, Punicic acid, or combination thereof;
- niacinamide; and
- L-aspartic acid.

20. The composition for suppressing deep seated fungal growth of claim 19, wherein the composition comprises the conjugated linoleic acid, Punicic acid, or combination thereof in a range between about 0.5% to about 70% of the composition, the niacinamide in a range between about 0.1% to about 30% of the composition; and the L-aspartic acid in a range between about 0.1% to about 30% of the composition.

* * * * *